United States Patent [19]

Ishikawa et al.

[11] Patent Number: 4,987,367
[45] Date of Patent: Jan. 22, 1991

[54] METHOD AND APPARATUS FOR PREDICTING DETERIORATION OF A MEMBER CONSTITUTING A PART OF EQUIPMENT

[75] Inventors: Yuichi Ishikawa, Mito; Toshihiko Yoshimura, Ibaraki; Tasuku Shimizu, Hitachi; Masahiro Otaka, Hitachi; Kazuo Takaku, Hitachi, all of Japan

[73] Assignee: Hitachi, Ltd, Tokyo, Japan

[21] Appl. No.: 406,366

[22] Filed: Sep. 12, 1989

[30] Foreign Application Priority Data

Sep. 16, 1988 [JP] Japan ................... 63-230010
Jan. 25, 1989 [JP] Japan ................... 01-13947

[51] Int. Cl.⁵ .............. G01R 33/12; G01N 27/72; G01N 23/225; G21C 17/00
[52] U.S. Cl. .................... 324/227; 324/223; 324/226; 324/235; 324/242; 324/248; 250/306; 376/249
[58] Field of Search ........ 324/209, 222, 227, 232–243, 324/248; 376/245, 249; 250/306

[56] References Cited

U.S. PATENT DOCUMENTS 4,692,701 9/1987 Dundas et al. ............ 324/209 X
4,881,030 11/1989 Stuecker et al. .......... 324/327 X

FOREIGN PATENT DOCUMENTS 28293 4/1973 Japan.
61981 5/1979 Japan.
12192 9/1979 Japan.
175947 10/1982 Japan.

OTHER PUBLICATIONS

Ishikawa, Yuichi; "A Microcomputer Based Prediction of The Probable Maximum Pit Depth on Pipelines by Means of Extreme Value Statistical Analysis", *Critical Issues in Reducing the Corrosion of Steels*, Mar. 1985, pp. 320–325 Editors H. Leidheiser, Jr. and S. Haruyama.

*Primary Examiner*—Gerard R. Strecker
*Attorney, Agent, or Firm*—Antonelli, Terry, Stout & Kraus

[57] ABSTRACT

Measurement of a physical property such as coercive force of a member to be inspected is performed at a plurality of locations in one region of the member. Similar measurement is performed in a plurality of different regions of the member and a maximum or minimum value (extreme value) is determined for each of the regions. On the basis of the extreme values thus determined, a recurrence period is determined in accordance with an extreme value statistic theory with the aid of a computer, whereon an estimated maximum value of the physical property of the member as a whole is determined from the recurrence period. On the basis of the estimated maximum value, the degree of deterioration of the member is predicted by the computer by consulting the data indicating the previously determined relation between the physical property and the degree of deterioration.

18 Claims, 18 Drawing Sheets

LOWERING IN IMPACT ENERGY
(DETERIORATION)

F I G. 18
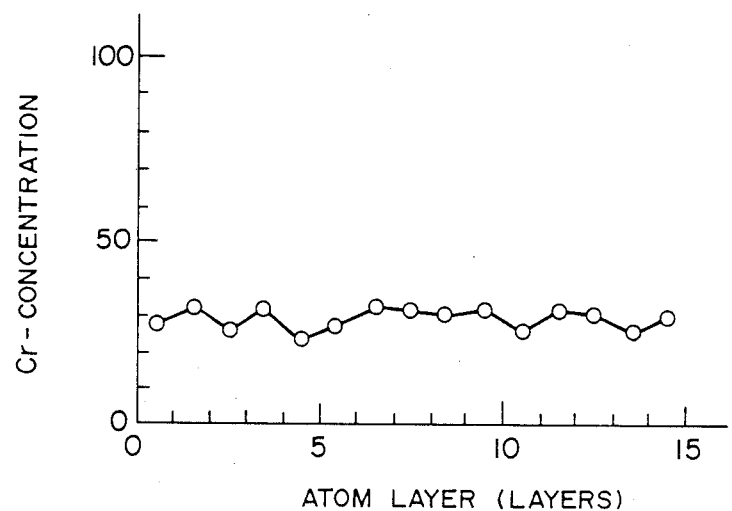
F I G. 19
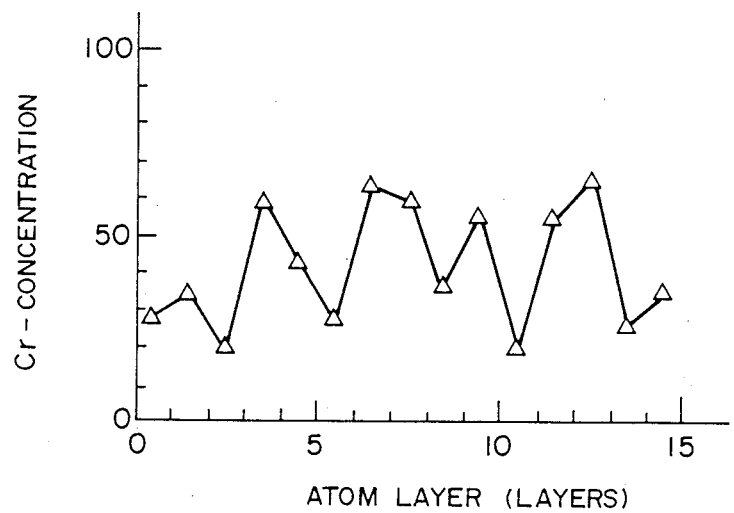

METHOD AND APPARATUS FOR PREDICTING DETERIORATION OF A MEMBER CONSTITUTING A PART OF EQUIPMENT

CROSS-REFERENCE TO RELATED APPLICATION

This invention is related to the U.S. Patent Application Ser. No. 247,414 filed Sept. 21, 1988 and assigned to the same assignee.

BACKGROUND OF THE INVENTION

The present invention generally relates to a method and an apparatus for predicting deterioration of a member constituting a part of a machine, apparatus, equipment or the like with the aid of a computer. More particularly, the present invention is concerned with a deterioration predicting method and apparatus which can profitably be used for prediction and/or detection of embrittlement, damage or injury of a member made of ferrite containing stainless steel and adapted to be operated or used in high temperature environments such as encountered in nuclear power plants, chemical plants or the like.

As a method of measuring embrittlement of a member or mechanical component (part) known heretofore in the art, there may be mentioned a method disclosed in JP-A-54-61981. According to this known method, embrittlement of stainless steel weld metals of austenite type is measured and the decision is made that embrittlement occurs when the content of δ-ferrite is decreased at least by 5% of the initial δ-ferrite content.

On the other hand, according to an inspection method for predicting the remnant use life of a member or part (mechanical component) exposed to a high temperature environment before it is ultimately destroyed, a specimen for test made of a same material as the member of concern of an existing machine, apparatus or equipment (hereinafter also referred to as the machine collectively) which is actually used or operated in a high temperature environment is hermetically disposed within a container in which a non-oxidizing atmosphere is maintained, wherein the electrical resistance of the specimen under test is measured in the state where the interior of the container is maintained at a substantially same temperature as that of the member of the existing machine to be inspected, to thereby predict the remnant use life of the member of concern by measuring the electrical resistance of the specimen under test. Reference may be made to JP-A-57-175947. To this end, a specimen of the same material as the member of the existing machine must be prepared separately.

Additionally, it is known to measure deterioration or degradation in the physical property of a low-alloy metal casting product such as a turbine casing which is brought about in the course of time lapse by disposing a specimen for test of the same material as the turbine casing within it. The specimen is taken out from the turbine casing after lapse of a predetermined period during which the specimen has been exposed to high temperature environment and then undergoes a test for determining the deterioration of the material forming the specimen. Reference may be made to JP-A-54-121192.

Besides, it is known to determine fatigue of a material by measuring the magnetic coercive force, as is disclosed in JP-A-48-28293. According to this known method, a specimen foil for test which is made of a material exhibiting the coercive force susceptible to variation with high sensitivity in dependence on the degree of fatigue of the material is affixed to a structural member of concern. Wherein variation in the coercive force of the specimen under test is measured through the medium of an electromagnet which is so designed and disposed as to generate magnetic force lines only in the surface of a portion of the member under inspection.

In the case of the last mentioned prior art method, no consideration is paid to differences existing between the member of the existing machine and the specimen tested such as, for example, differences in stress distribution, temperature distribution, internal texture and presence or absence of radioactive irradiation, thus giving rise to a problem in respect to the accuracy and reliability of the estimation of deterioration of the existing mechanical member due to the aging on the basis of the data obtained from the measurement of the separately provided test specimen.

It is further noted that the methods known heretofore are incapable of detecting accurately or precisely the state of embrittlement without the need for overall inspection of a member of concern and proved impractical for the inspection of the member as a whole when the member is difficult to access or when the area to be inspected is excessively large, as in the case of machines installed in nuclear power plants or chemical plants.

SUMMARY OF THE INVENTION

It is therefore an object of the present invention to provide a method and apparatus for predicting with increased accuracy and improved reliability the deterioration or embrittlement of a member constituting a part of an existing apparatus and made of ferrite containing stainless steel and used in high temperature environments such as encountered in chemical plants or nuclear power plants, the deterioration or embrittlement being brought about due to aging under exposure to a high temperature.

Another object of the present invention is to provide a deterioration predicting apparatus imparted with capability of sampling a part of material forming a member of concern in an existing machine or apparatus or equipment of the plant without exerting any influence to the latter.

It is still another object of the present invention to provide a deterioration predicting apparatus capable of predicting non-destructively with a high accuracy within a short time even the initial state or symptom of deterioration of machines or apparatuses operated in high temperature environments.

In view of the above and other objects which will be more apparent as description proceeds, there is provided according to a general aspect of the present invention a system for evaluating deterioration of machinery by detecting changes in a magnetic property of a material as brought about by aging (i.e. deterioration taking place in the course of time lapse), wherein the concept of recurrence period based on a statistical distribution of extreme values of the measured changes in the magnetic characteristic determined for a given number of regions of a machine under inspection is utilized for estimating the maximum or minimum value of the change in the magnetic characteristic for the whole machine. Wherein the maximum value of deterioration in the machine is predicted on the basis of the estimated value by referencing previously prepared data which indicate relationship between the deterioration of the material and the change in the magnetic characteristic thereof.

More specifically, a plurality of regions of a machine to be inspected are accessed by a magnetic sensor or the like to apply a magnetic field, wherein magnetization is detected to measure a relation existing between the intensity of the magnetic field as applied and the magnetization as induced for each of the regions. In this manner, magnetic characteristic parameter such as, for example, the coercive force is detected for the accessed region by scanning over a predetermined area with a sensor or by using an array type sensor assembly to thereby determine the extreme value (maximum value in the case of the coercive force) for each of the accessed regions. As is known in the art, the statistical distribution of the extreme values thus determined can be approximated by the double-exponential distribution. Accordingly, the maximum value or minimum value for a machine as a whole can be predicted by using the concept of the recurrence period T of the extreme value statistical analysis without need for performing the measurement for the whole machine. On the basis of the predicted extreme value for the machine as a whole, the maximum degree of deterioration of the machine under inspection is determined by consulting the previously prepared data indicating the relation between the degree of deterioration of material and change in the magnetic characteristic thereof.

Goodness of correspondence can be observed between the change in the magnetic characteristic typified especially by the coercive force and the Barkhausen noise output of ferromagnetic phase which makes appearance as phase decomposition proceeds in the course of time lapse on one hand and the lowering in the impact energy (impact strength) indicating the degree of deterioration. Accordingly, these physical characteristics can also be made use of in carrying out the present invention.

In order to apply efficiently the magnetic field to an object for inspection, it is conceived to use a coil of a superconducting material as the excitation coil. For measuring the Barkhausen noise with a high accuracy, the use of a superconducting quantum interference device or SQUID sensor and an acoustic emission measuring device is preferred.

Alternatively, determination of delicate change in the composition of the material forming a region of concern by an atom probe method is equally effective and advantageous in carrying out the invention.

In a metal material containing ferromagnetic phase, the latter undergoes phase decomposition in the course of use in a high temperature environment for an extended time, as the result of which fluctuation in alloy concentration in a very small region becomes remarkable, as shown in FIGS. 2 at (a), (b) and (c) of the accompanying drawings, ultimately giving rise to appearance of precipitates. Further, impurities such as sulfur, phosphor and the like are concentrated at grain boundaries. In the course of progress of these phenomena, changes in the mechanical properties such as increasing in hardness, lowering of impact energy (impact strength) take place.

After extensive studies concerning embrittlement of ferrite containing stainless steel material under heating at a high temperature, the inventors have discovered that the changes in the mechanical properties mentioned above are ascribable to precipitation of $\alpha'$ (alpha prime) phase of high Cr-concentration due to decomposition of the ferrite phase ($\alpha$). Further, it has also been observed that magnetic properties of stainless steel are caused to change significantly by separation of ferromagnetic ($\alpha$) phase and non-ferromagnetic phase ($\alpha'$).

The process of phase decomposition proceeds extremely randomly in respect to space and time. In other words, the event of phase decomposition exhibits inherently the nature of probability. Accordingly, the change in the magnetic property brought about by the phase decomposition can not evade the nature of probability and hence dispersion. By processing statistically the dispersion, it is possible to predict quantitatively the degree of deterioration of a machine. In most cases, the life of a machine is determined by local embrittlement of high degree rather than average embrittlement of the machine as a whole. In view of this fact, the statistic processing by taking advantage of the extreme value (maximum or minimum value), i.e. the extreme value statistic analysis can be adopted effectively and advantageously.

For achieving the objects mentioned hereinbefore, it is further proposed according to another aspect of the invention that a surface material of a mechanical member constituting a part of an existing machine, apparatus or equipment in a nuclear power plant is sampled by using a dental drill, wherein pulverized material (powder or drillings) produced by drill machining is recovered by a floating type concentration unit through an underwater pump, with the drilled portion being polished by a grinder.

For preventing the pulverized drillings from dropping to the bottom of the nuclear reactor, it is preferred that a part of specimen sampling container brought into contact with a member of concern of an existing machine upon operation should be formed of rubber. Further, an injection port for a high-pressure nitrogen gas should be installed in the specimen sampling container, which may further include a vacuum pump equipped with a gate valve.

With a view to allowing the pulverized drillings to be definitely separated from materials floating on the water surface within the reactor to thereby enhance the accuracy and reliability of analysis of the recovered specimen, the specimen sampling container may include a guide tube and a filter for eliminating the materials floating on the water surface within the reactor.

A water jet and ultrasonic cleaner may be employed for removing clads formed on the wall surface of duplex-phase stainless steel material.

The internal structure or texture of the recovered powder may be observed by using an atom probe and a transmission electron microscope. Besides, the magnetic characteristics of the recovered drillings may be inspected by using the SQUID sensor.

In case a plant to be inspected according to the teaching of the present invention is a nuclear power plant, the specimen sampling container is disposed in the vicinity of the reactor vessel wall, whereon clads and oxide films formed on the reactor wall of duplex-phase stainless steel are removed by using the water jet. Subsequently, reactor water (coolant) and the removed clad material as well as oxide films are flushed from the container by injecting the nitrogen gas of high pressure for preventing the clad materials and the oxide films from being recovered. Further, a container for the vacuum pump isolated by the gate valve is filled with high-pressure nitrogen gas, whereon the outermost wall surface of duplex-phase stainless steel is machined by means of the dental drill. Subsequently, the gate valve is opened to evacuate the whole container, whereby the drillings are carried by the nitrogen gas to the vacuum pump to be ultimately recovered. Thereafter, the gate valve is closed and the drilled portion is polished by the grindwheel to thereby remove the crack from the wall surface. Since the vacuum prevails within the container, there is no danger of the drillings dropping to the bottom of the nuclear reactor. Of the recovered drillings, only those containing ferrite phase having ferromagnetism and playing a role in the deterioration are selectively separated by using an electromagnet and sorted on the size base by a multi-stage filter. The specimen obtained in this manner can be observed by a transmission electron microscope. Through analysis of the specimen by the atom probe method, it is possible to determine the compositions and the sizes of very fine precipitates of $\alpha'$-phase, G-phase and others in the ferrite phase.

It is also possible to detect fine changes in the physical properties by means of the SQUID sensor to thereby determine the change in the magnetic properties.

Goodness of correspondence is found between the changes in the magnetic characteristics typified by the coercive force and the Barkhausen noise output of ferromagnetic phase of metal material brought about by aging on one hand and the lowering of impact energy indicating the deterioration.

In the metal material containing ferromagnetic elements, the ferromagnetic phase undergoes phase decomposition in the course of time lapse during the use in a high temperature environment, resulting in significant fluctuation in the alloy concentration in a very small region, which ultimately gives rise to appearance of precipitates. Besides, sulfur, phosphor and other impurities are concentrated at the grain boundaries. Thus, change will occur in the mechanical properties such as increase in hardness and lowering of the impact energy.

BRIEF DESCRIPTION OF THE DRAWINGS

FIG. 18 is a characteristic diagram showing a profile of Cr-concentration in ferrite phase of unaged duplex-phase stainless steel;

FIG. 19 shows a profile of Cr-concentration in ferrite phase of stainless steel undergone aging at a temperature of 475° C. for 1000 hours;

DESCRIPTION OF THE PREFERRED EMBODIMENTS

Now, the present invention will be described in detail in conjunction with exemplary or preferred embodiments thereof by reference to the accompanying drawings.

Figure 1:
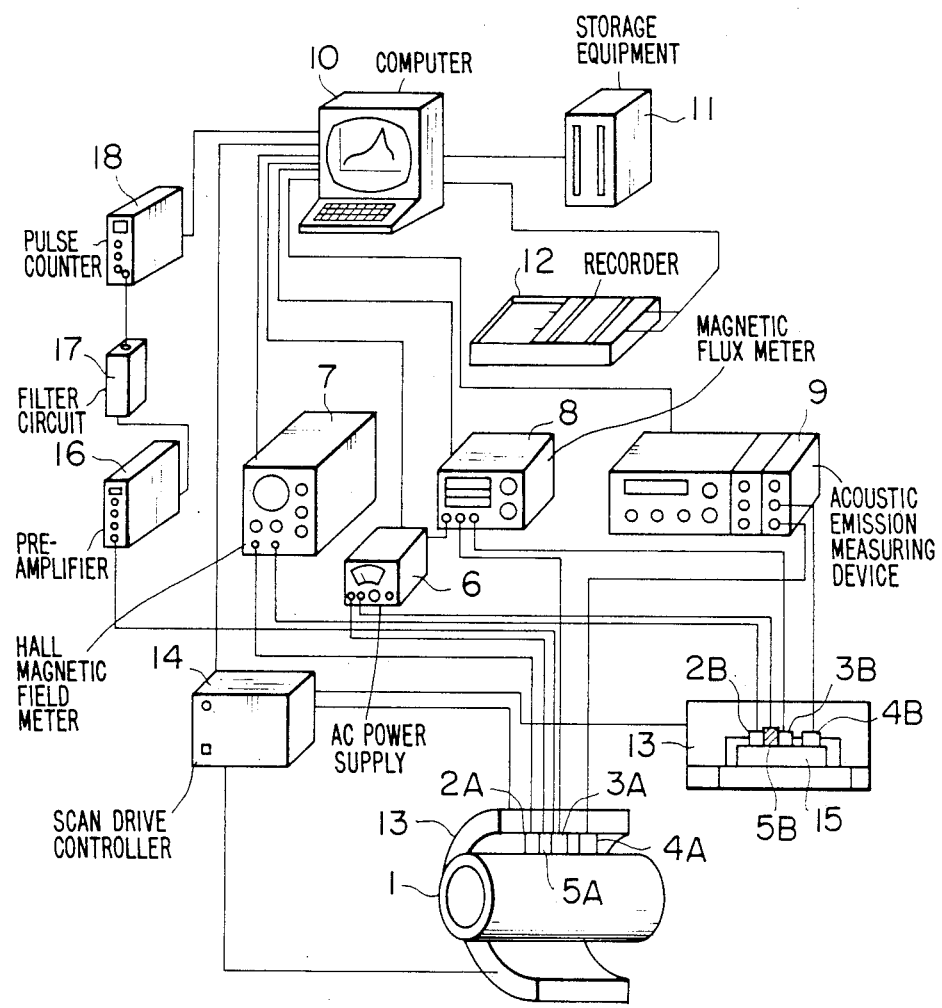
FIG. 1 is a pictorial view showing, by way of example only, a general arrangement of a system for carrying out a method of predicting deterioration of metallic materials according to an exemplary embodiment of the invention.
Figure 2:
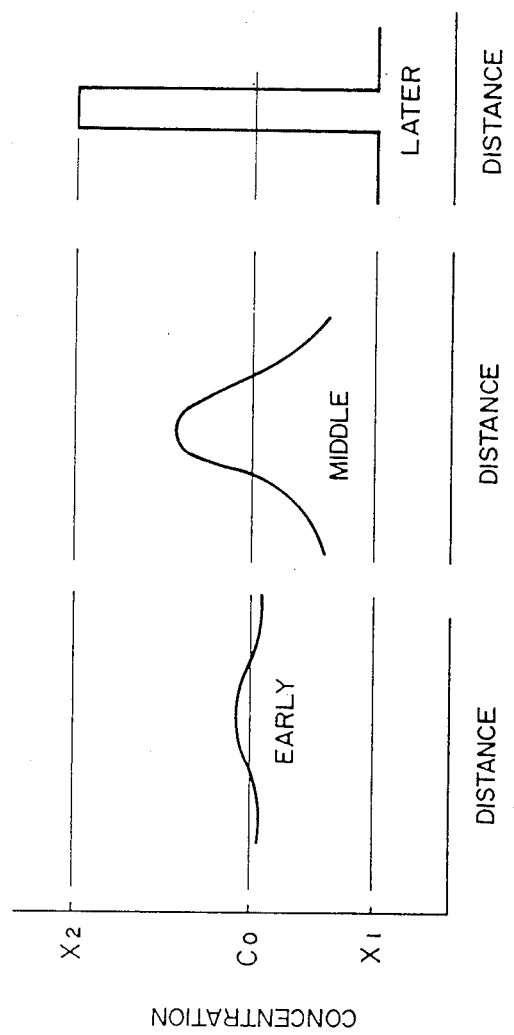
FIGS. 2(a) through (c) are characteristic diagrams illustrating graphically extremely fine phase decomposition of ferrite phase in terms of fluctuations in alloy concentration.

FIG. 1 is a pictorial view showing, by way of example only, a general arrangement of a system for carrying out a method of predicting deterioration of metal materials according to an exemplary embodiment of the invention. In the figure, a reference numeral 1 denotes a pipeline installed in a nuclear power plant which constitutes the object for the measurement. Reference characters 2A and 2B denote Hall elements, 3A and 3B denote coils, 4A and 4B denote transducers for measurement of acoustic emission, 5A and 5B denote excitation coils, 6 denotes an AC power supply, 7 denotes a Hall element type magnetic field meter, 8 denotes a magnetic flux meter, 9 denotes an acoustic emission measuring device, 10 denotes a computer, 11 denotes external storage equipment, 12 denotes an external recorder unit, 13 denotes a scan drive unit for various sensors and/or detectors, 14 denotes a scan drive controller, 15 denotes a reference specimen for test, 16 denotes a preamplifier, 17 denotes a filter circuit and 18 denotes a pulse counter.

There are disposed on the surface of the object or pipeline 1 under inspection the Hall element 2A adapted to serve for detecting the magnetic field, the coil 3A for detecting the magnetization, the transducer 4A for measuring the acoustic emission and the excitation coil 5 for applying a magnetic field. On the other hand, the reference specimen for test 15 has a surface on which there are disposed the Hall element 2B, the coil 3B, the acoustic emission measuring transducer 4B and the excitation coil 5B. An electric motor constituting a major part of the scan drive unit 13 as well as other drive units and signal systems are connected to the scan drive controller 14 to be controlled by the latter. Parenthetically, it should be mentioned that the test reference specimen 15 is used only for the purpose of calibrating the magnetic characteristic values as measured and does not constitute any essential part indispensable for the implementation of the invention.

The coils 5A and 5B are connected to the AC power supply 6 of a variable frequency and each can generate an excitation magnetic field having a sinusoidal waveform at a desired frequency. The intensity of the magnetic field H is detected by the Hall elements 2A and 2B disposed in the vicinity of the magnetic gaps, respectively. The Hall elements 2A and 2B are connected to the magnetic field meter 7. The magnetic flux is detected in the form of AC voltages induced in the coils 3A and 3B wound closely around the pipe 1 to be inspected. The signal generated by the detection coil 3A in response to the Barkhausen effect is amplified by the preamplifier 16 and inputted to the pulse counter 18 by way of the filter 17, whereby only the signals having magnitudes greater than a predetermined threshold value are measured.

With the arrangement outlined above, magnetic hysteresis curves and the succession of discontinuous changes in magnetization ascribable to the Barkhausen effect which takes place due to movement of the domain wall can be measured.

On the other hand, the sound generated by the Barkhausen effect is measured by the transducers 4A and 4B destined for measuring the acoustic emission. The transducers 4A and 4B are connected to the acoustic emission measuring unit 9 which incorporates therein a frequency analyzer. It should here be mentioned that with the present invention, it is contemplated to measure only one type of physical property. Measurement of a variety of physical characteristics mentioned above in conjunction with FIG. 1 is not necessary.

Use of a SQUID sensor as the magnetic flux meter 8 can assure a high accuracy for the measurement.

Figure 3:
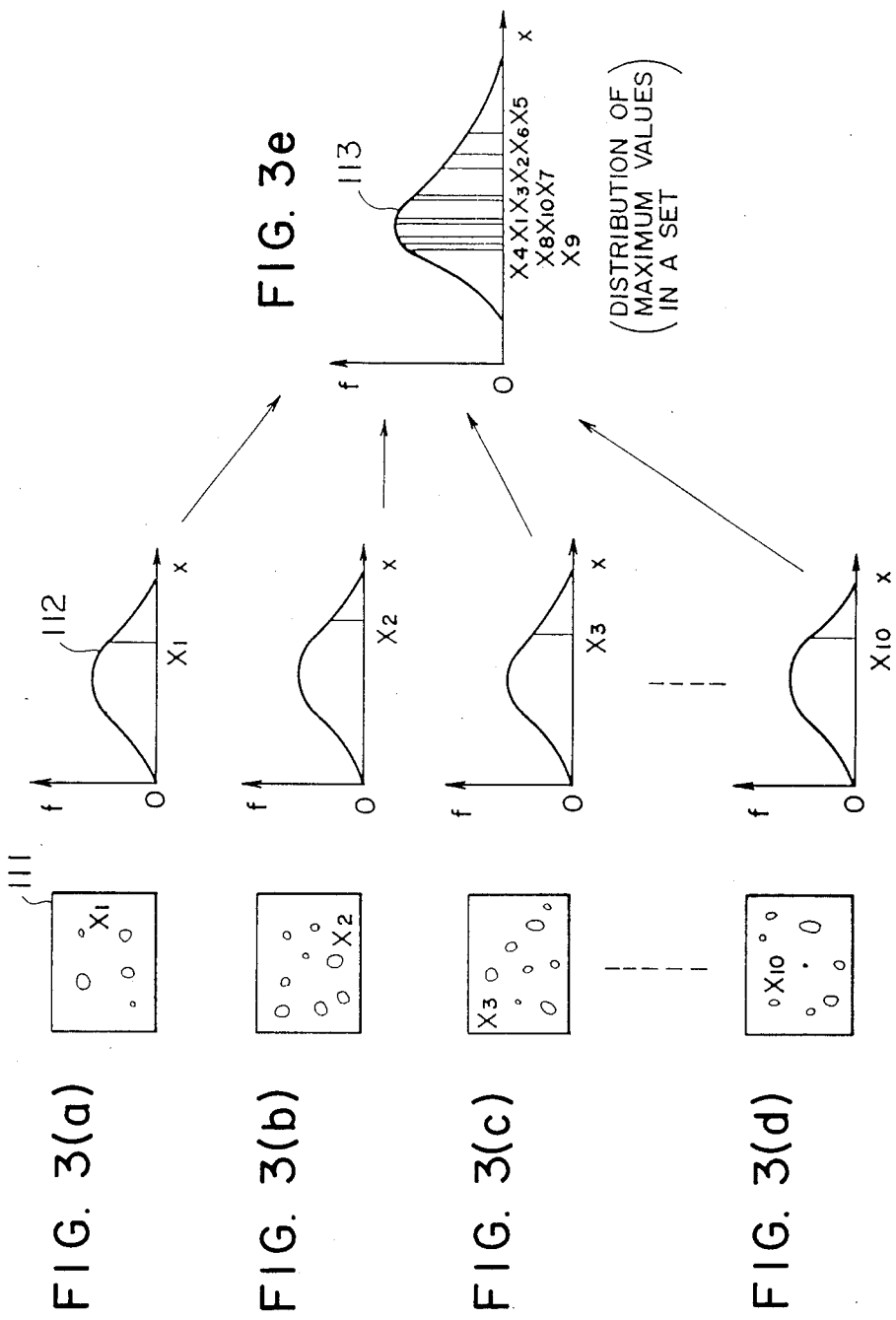
FIGS. 3(a) through (c) show views for illustrating the concept underlying the extreme value statistical distribution analysis.

Now, the principle underlying the present invention will be elucidated by reference to FIG. 3.

FIGS. 3(a) through (e) show views for illustrating the concept of the extreme value statistical distribution analysis. In the figures, dispersion in magnitude of the values measured at the individual regions where measuring devices are installed, respectively, is shown at 111, while fundamental distributions of the values measured at the respective regions are indicated by curves 112. Further, a distribution of extreme values (maximum values in this case) extracted from the distributions 112 is shown in FIG. 3(e) at 113, where $X_1, X_2, X_3, \ldots, X_{10}$ represent the maximum values measured at the individual regions, respectively. According to the extreme value statistics, a set of the extremal values (i.e. set of maximum values or minimum values) at the individual regions can be approximated by the extreme value distribution of double-exponential distribution type, so far as the foot portion of the fundamental distribution curves can be represented by the exponential distribution curve.

Considering the double exponential distribution of the maximum values (extreme values), by way of example, each maximum value (extreme value) can be represented by the following distribution function:

$$F(X) = \exp\left\{ -\exp\left( -\frac{X-\lambda}{\alpha} \right) \right\} \quad (1)$$

where $\alpha$ and $\lambda$ represents a scale parameter and a position parameter, respectively, known in the field of statistics.

A quantity employed for predicting the maximum value $X_{max}$ for a machine as a whole on the basis of the maximum values (extreme values) measured at the individual regions is known as the recurrence or return period T which is given by the ratio between the total area (A) of the object for which the prediction is intended and the area (Al) of each of the regions for measurement, as follows:

$$T = A/A_1 \quad (2)$$

The maximum value $X_{max}$ is given as a function of T, $\lambda$ and $\alpha$ according to the extreme value statistic theory. Namely, $$X_{max} = \lambda + \alpha \ln T$$

Figure 4:
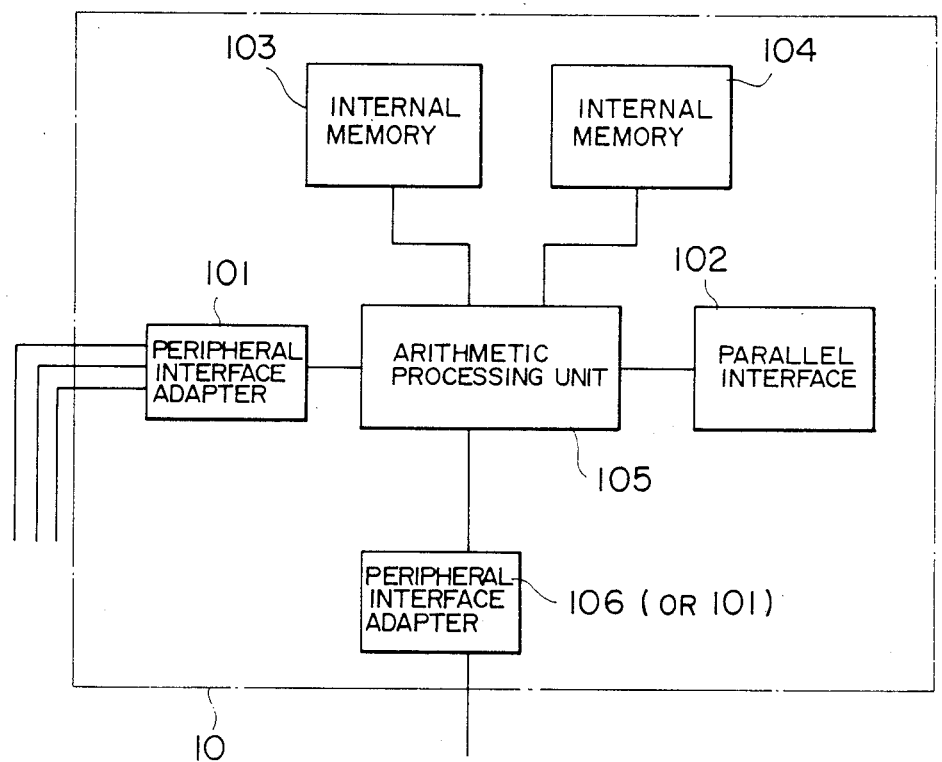
FIG. 4 is a block diagram showing, by way of example, a structure of the computer employed in the system shown in FIG. 1.

FIG. 4 shows in detail a structure of the computer 10. As can be seen from this figure, the computer 10 is provided with a peripheral interface adapter 106 for controlling the scan drive controller 14 and the AC power supply 6, an interface 101 for enabling the magnetic flux meter 8, the acoustic emission measuring instrument 9 and the pulse counter 18, and a parallel interface 102 for interconnection with the external storage equipment 11 and the external recording unit 12. Further, the computer 10 includes an internal memory 103 for storing data base to be utilized for evaluation of deterioration of the metal materials, an internal memory 104 which stores a program for processing statistically the data resulting from the measurements and a program for arithmetically determining the degree of deterioration on the basis of the data base and the statistically processed measurement data, and an arithmetic unit 105 for performing arithmetic operations on the data in accordance with the programs mentioned above. In another embodiment of the present invention, the peripheral interface adapter 106 may be replaced by the interface 101 destined for the data transaction.

Description will now be directed to a procedure for detecting the degree of deterioration of a ferrite containing stainless steel material exposed to a high temperature of 290° C. with the aid of the apparatus having the structure implemented as described above.

At first, the scan drive unit 13 is disposed on the surface of the pipe 1 under inspection at a weld region and positioned at the origin of the measuring system, whereon the computer 10 designates the range for inspection. The scan drive unit 13 is moved to a point where measurement is to be started, while the A.C. power supply source 6 supplies to the scan drive unit 13 an excitation current of sinusoidal waveform with a frequency and an amplitude commanded by the computer 10.

The magnetic hysteresis curve can be determined on the basis of the measurements outputted from the Hall element 2A and the detection coil 3A to be displayed on a display unit of the computer 10, whereon the coercive force $H_c$, residual magnetic flux density $B_R$ and the initial permeability $\mu$ can be determined. Further, in connection with the Barkhausen effect, magnetization is measured in terms of the output of the detection coil 3A, while the output sound is fetched in terms of the output of the transducer 4A, whereon count rate dN/dt, total pulse number $\int N(H)dH$, and a pulse height spectrum N(E) are determined, respectively. The welded portion of the pipe is measured stepwise by an increment corresponding to the size (2 mm×2 mm) of the detection coil. Upon completion of the measurement along the whole circumferential weld, the scan drive unit 13 is moved to a weld region to be next measured. In this manner, the measurement is conducted for all the predetermined weld regions. Upon completion of the measurement for the last weld region, the measurement data are again loaded into the computer from the external storage equipment 11 to be processed statistically, the results of which are then subjected to comparison with the data base prepared previously for thereby determining the degree of deterioration of the material.

Next, description will be made of a procedure for predicting the maximum value of deterioration in all the welds of the pipe on the basis of the data obtained from the measurement.

Figure 5:
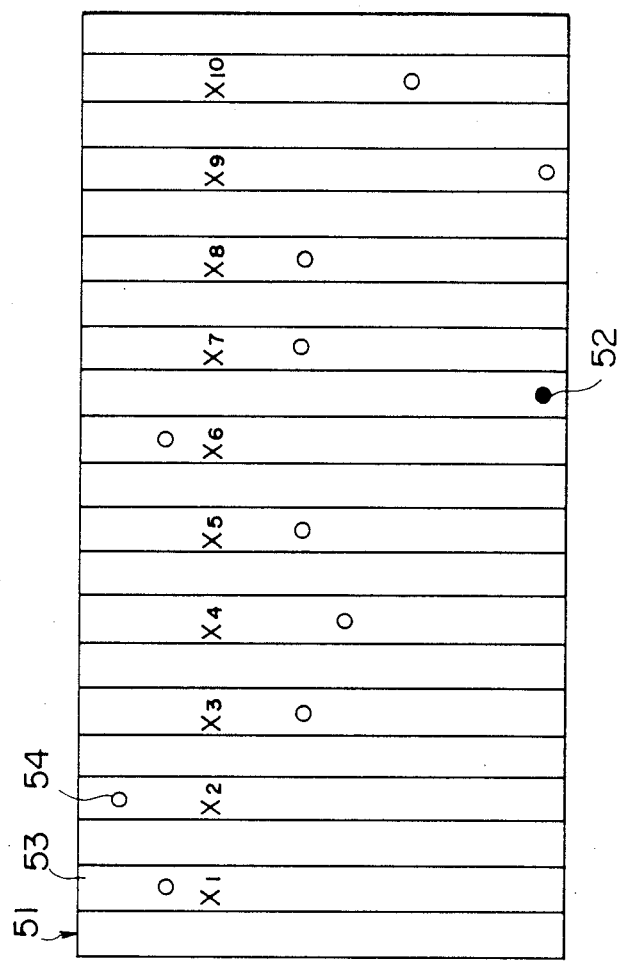
FIG. 5 is a schematic view for illustrating relations between extreme values in the welds of a pipe line and a maximum value in all the welds thereof.
Figure 6:
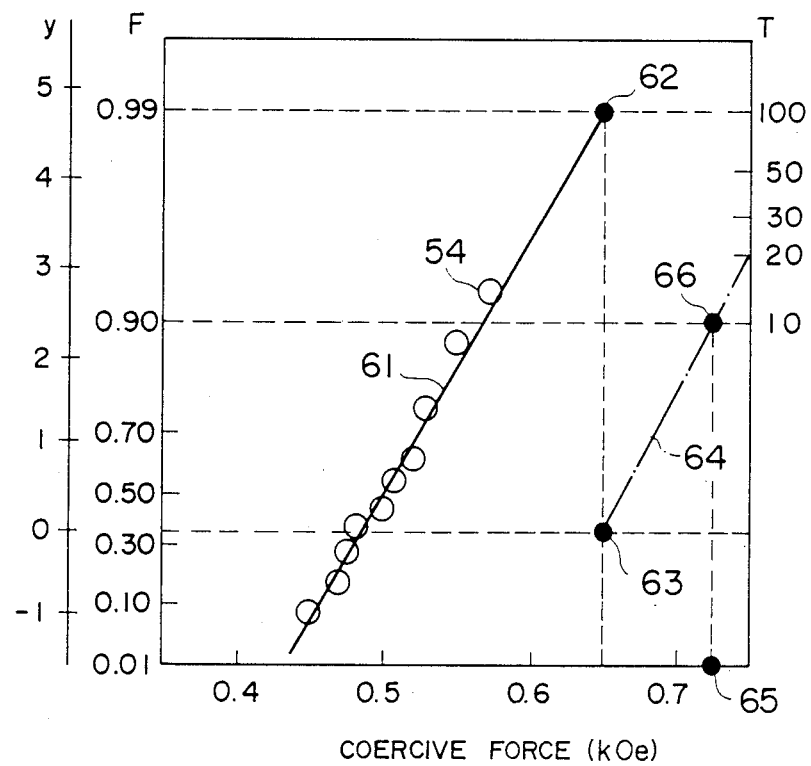
FIG. 6 is a characteristic diagram for illustrating graphically a method of predicting the maximum value of the extreme values of welds distributed in a double-exponential form by an extreme value statistical analysis.

FIG. 5 shows in a circumferentially exploded view all the weld regions of a pipeline for which prediction should be made as to the deterioration with all the weld regions being shown interconnected. In this figure, a region shown in the form of an elongated rectangle represents one weld region. The maximum value 54 of the measurement in all the weld regions 51 is shown in a solid circle in black. Further, in this figure, $X_1, X_2, \ldots, X_{10}$ represent the maximum (extreme) values measured in ten weld regions, respectively. It should be noted that the maximum (extreme) values $X_1, X_2, \ldots, X_{10}$ represent the maximum measured values at ten weld regions, respectively. The maximum (extreme) values $X_1, X_2, \ldots, X_{10}$ of the coercive forces determined from the magnetic hysteresis curves (i.e. the curves representing changes in magnetization brought about by application of the magnetic field) are calculated by the computer in accordance with the extreme value statistic analysis procedure. FIG. 6 illustrates the results of the manual potting of the maximum (extreme) values on a recording sheet referred to as the extreme value probability sheet. This can be accomplished by arraying the maximum (extreme) values $X_1, X_2, \ldots, X_{10}$ in the increasing order and plotting the values of F (i.e. the individual maximum or extreme values) along the y-axis in accordance with the following expression:

$$F = i/(n+1) \tag{4}$$

where i represents the ordinal number of the data in the sequence of small to large values of the data (i=1, 2, 3, ...) and n represents the total number of the data.

By drawing a straight line 61 along the plotted points of the individual maximum (extreme) values by eye measure (i.e. at a rough estimate) or in accordance with the least square method and extrapolating the plotted points along the right ordinate scale T on the probability paper for all the weld regions (up to T=100 in the case of the illustrated example), the maximum value 62 of the coercive force can be determined. This is the largest value of the coercive force predicted for all the weld regions of the pipe. Further, in case the design use life of an existing mechanical component determined in consideration of deterioration is available in terms of the design tolerance value of the coercive force, an intersection 63 between the line representing the largest coercive force and a line representing the left ordinate y equal to zero is determined, whereon a single-dot line 64 is drawn from the origin given by the point 63 in parallel with the straight line 61, and the probability P of the mechanical component of concern reaching the use life thereof is determined on the basis of the intersection 66 between a line representing the design tolerance value 65 and the single-dot line 64 in accordance with the following expression:

$$P = 1 - F \tag{5}$$

For imparting a safety factor to the predicted value 62 of the largest or maximum coercive force, a corrosion life predicting method based on the extreme value statistical analysis will be effective. Furthermore, the predicted value 62 representing the largest coercive force can also be determined by resorting to other methods such as a maximizing sequence, a minimum fraction unbiased estimator method in addition to the method of using the probability paper and the least square method mentioned above. According to the invention, these procedures can be carried out by the computer. In conjunction with the extreme value statistical analysis, reference may be made to "A MICROCOMPUTER BASED PREDICTION OF THE PROBABLE MAXIMUM PIT DEPTH ON PIPELINES BY MEANS OF EXTREME VALUE STATISTICAL ANALYSIS", Mar. 1985, pp. 320-325.

Figure 7:
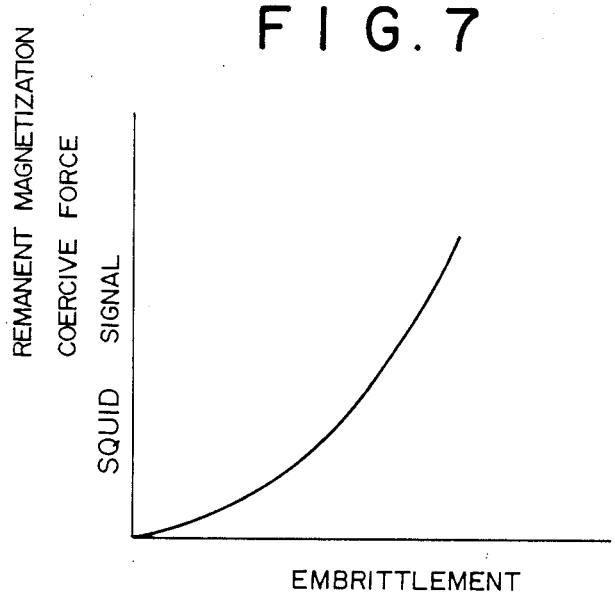
FIG. 7 is a characteristic diagram showing a calibrated curve which represents a relation between coercive force and embrittlement (a measure of deterioration)

There exists between the degree of deterioration or embrittlement in the impact strength and the coercive force of the ferrite containing stainless steel material such a relation as illustrated in FIG. 7. It is thus possible to predict the degree of embrittlement or deterioration of mechanical components made of the abovementioned material on the basis of the maximum or largest value of the coercive force determined through the procedure described above. Of course, the degree of embrittlement or deterioration can equally be predicted through the abovementioned procedure by determining the maximum value of the magnetic output or acoustic output of the Barkhausen noise in place of the maximum value of the coercive force. Besides, there can effectively be made use of measurements of the remnant magnetization, permeability, magnetic isotropy or magnetostriction.

Figure 8:
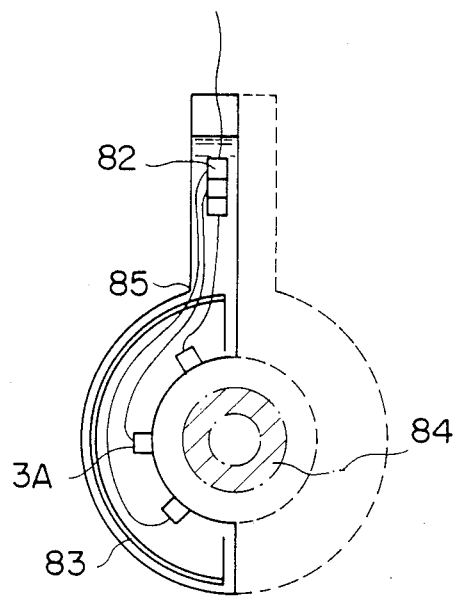
FIG. 8 is a schematic sectional view taken in the vicinity of an object for inspection and showing a structure of an apparatus for carrying out a method according to another embodiment of the invention.

FIG. 8 shows a further embodiment of the present invention. According to the teaching incarnated in this embodiment, a plurality of detection coils 3A are disposed circumferentially, wherein the maximum (extreme) value is determined from the outputs of the plural detection coils without scanning the weld regions of the pipeline along the whole circumference. For measurement of the magnetic flux, a SQUID sensor 82 is employed. Disposed within a cooling container 85 shown with a half in section the detection coils 3A and a magnetic shield 83. In this case, the maximum value of concern in all the weld regions of the pipeline is determined by the return or recurrence period T given by the following expression:

$$\left( \begin{array}{c} \text{area of weld/area of} \\ \text{detection coil} \end{array} \right) \times \text{(number of welds of pipe)}$$

Figure 9:
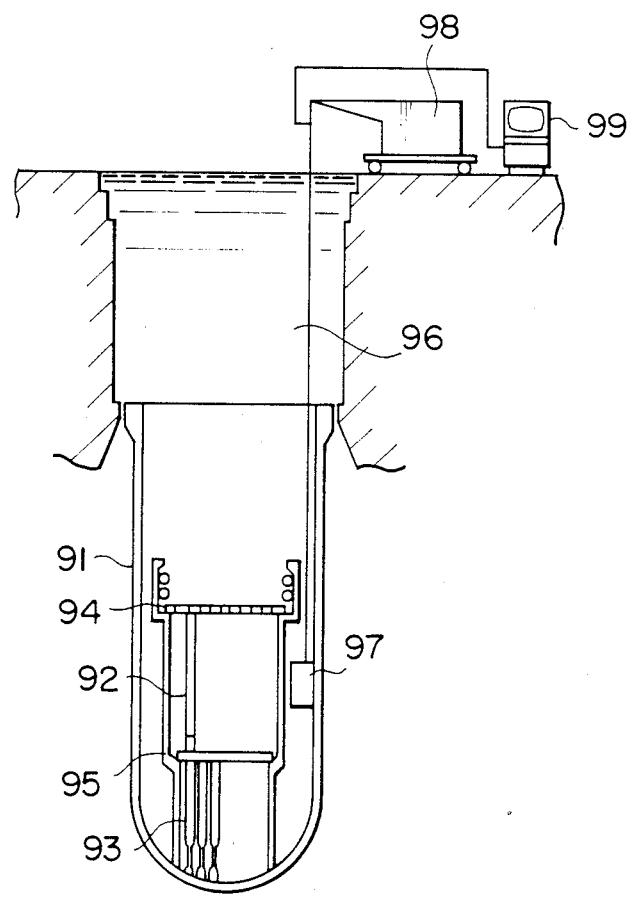
FIG. 9 is a schematic view showing an internal structure of a nuclear reactor pressure vessel together with another embodiment of the apparatus according to the invention.

FIG. 9 is a schematic view showing an internal structure of a nuclear reactor pressure vessel in a nuclear power plant and disposition of a specimen sampling apparatus according to an embodiment of the present invention. More specifically, in FIG. 9, a reference numeral 91 denotes a pressure vessel of a nuclear reactor, 92 denotes a control rod assembly, 93 denotes control rod guide thimbles, 94 denotes a top grid, 95 denotes a reactor core support, and 96 denotes a reactor coolant. Since duplex-phase stainless steel material from which the mechanical components of the nuclear plant are actually made is used for an extended time in a high temperature environment, micro-precipitates are produced in the ferrite phase of duplex-phase stainless steel due to the aging at a high temperature, whereby the strength of the mechanical component or member is degraded remarkably. It goes without saying that such degradation in the strength of the material constituting the mechanical component limits the use life of the power plant as a whole.

For measuring the characteristic value of the material strength as well as those of the interior of the reactor, it is necessary to sample parts of the existing mechanical components by a dispersion ring sampling method without affecting the actual structural strength of the mechanical components. The specimen sampling unit 97 is designed to sample an extremely small amount of specimen from the surface of the reactor enclosure wall of the nuclear reactor pressure vessel 91. The specimen sampling unit 97 is suspended by a crane 98 to be disposed in the vicinity of the reactor wall surface so that the specimen sampling operation can visually be observed on a monitor 99 through a fiber scope incorporated in the specimen sampling unit 97.

More specifically, a magnetism characteristic measuring unit 97' (not shown) is suspended by the crane 98 to be disposed within the vessel for the purpose of predicting the deterioration of stainless steel constituting a liner for the inner wall of the nuclear reactor pressure vessel at a plurality of given regions. In this connection, it will be convenient to use a sensor array constituted by a plurality of detection coils disposed in a plane in a matrix-like array for determining simultaneously the maximum (extreme) values in the region under inspection.

Figure 10:
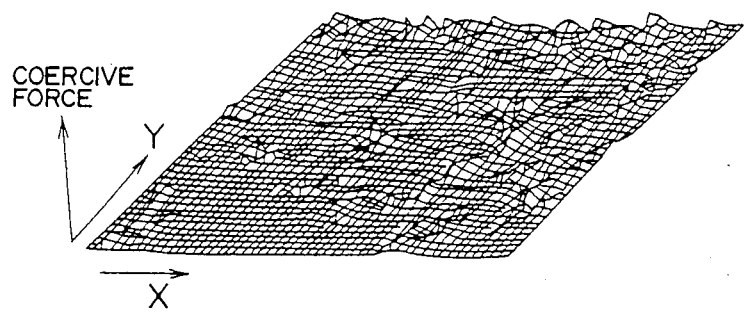
FIG. 10 shows a three-dimensional graph as an example of display of the measured coercive force values obtained by scanning over a predetermined region with a magnetic sensor.

FIG. 10 is a three-dimensional graph showing distribution of coercive force values obtained by scanning a predetermined region with a magnetic sensor. Symptoms of deterioration can clearly be observed in the form of increases in the coercive force. When the sensor array mentioned above is employed, it is preferred to display the outputs of the individual sensors in terms of differences in color density as in the case of a light and shade diagram.

Figure 11:
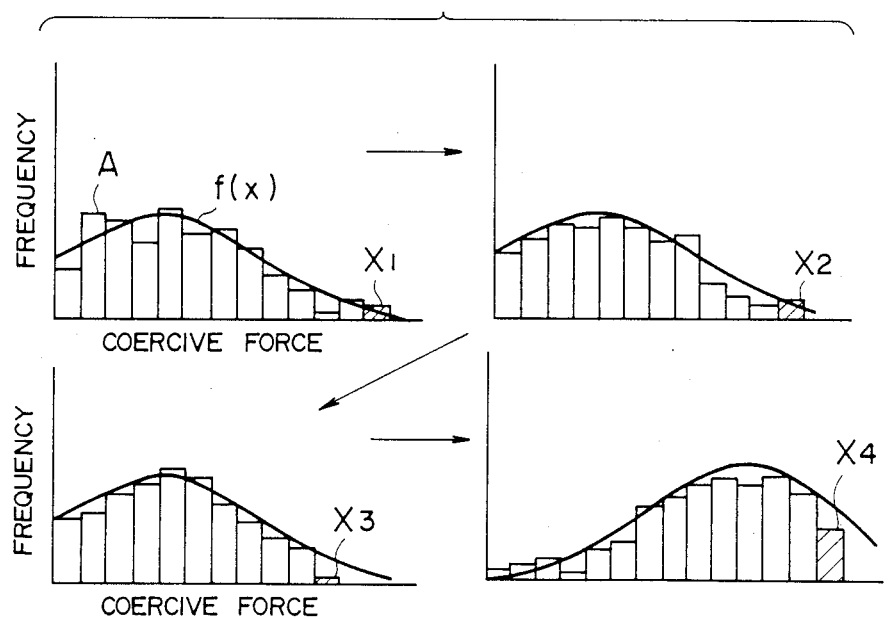
FIG. 11 is a view showing in histograms the individual values measured by the scanning method.

FIG. 11 is a view showing in histograms the individual values measured by the scanning method or by employing the sensor array. It is possible to examine the validity of application of the extreme value statistical analysis by comparing the frequency distribution A and the density function f(x). Difference of the distribution profile $X_4$ from others $X_1$, $X_2$ and $X_3$ suggests the presence of abnormality in the data distribution $X_4$. Accordingly, measurement is then performed for those regions which surround the region exhibiting the abnormal data distribution $X_4$. According to the invention, the relevant processings can be performed by the computer.

Figure 12:
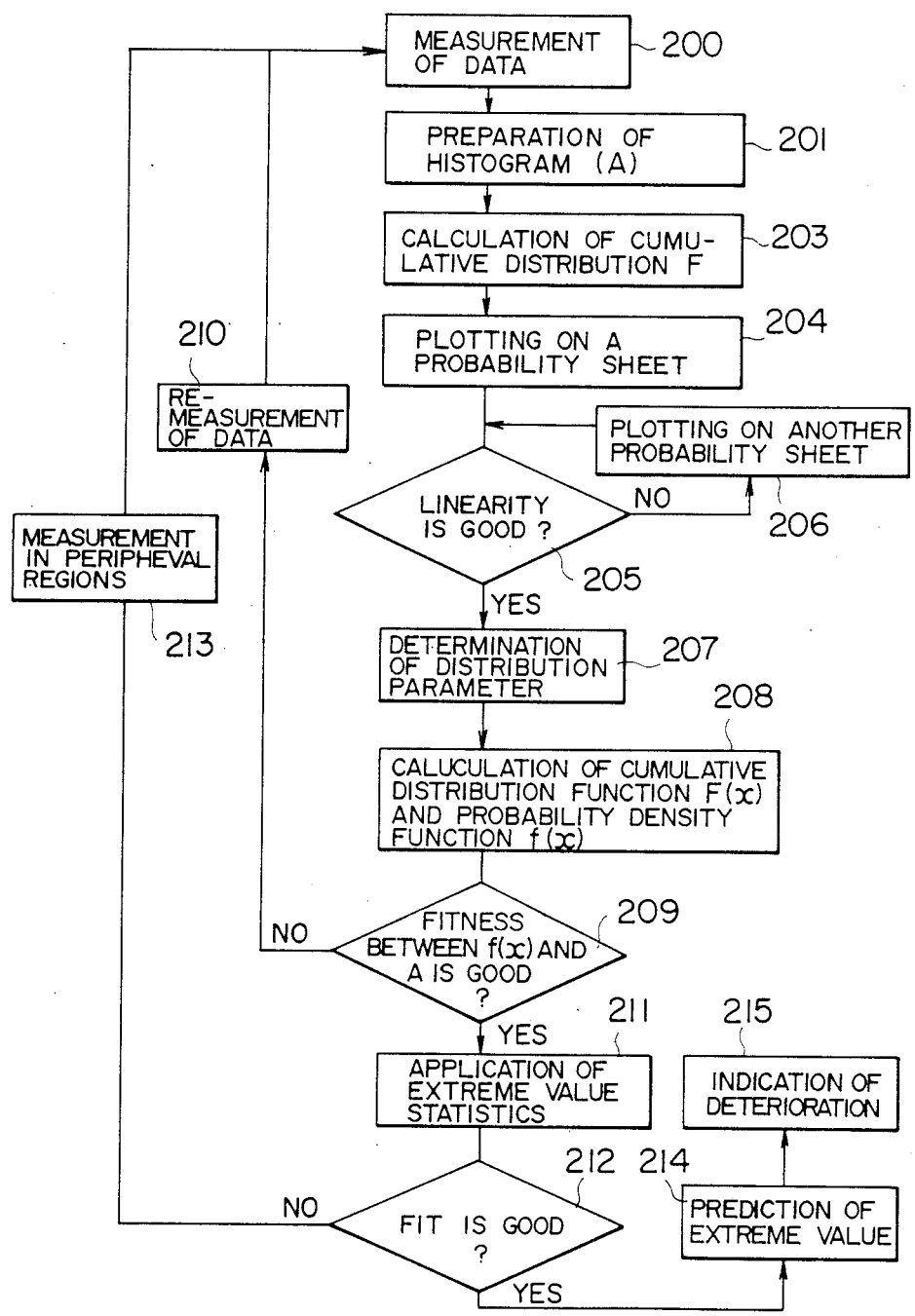
FIG. 12 is a flow chart for illustrating procedure for predicting the maximum value of deterioration with the aid of a computer by applying the extreme value statistic analysis.

FIG. 12 is a flow chart for illustrating procedure for predicting the maximum value in the degree of deterioration with the aid of the computer according to the extreme value statistic theory.

Referring to FIG. 12, a histogram (A) is prepared in accordance with magnitudes of the measured values (step 201), whereon a cumulative distribution F is arithmetically determined in accordance with $F=1/(n+1)$ (step 203), the result of which is plotted on an appropriate probability sheet (step 204), and the goodness of fit of linear approximation is examined (step 205). If it is good, the parameter of the distribution is determined (step 207), being followed by calculation of a cumulative distribution function $F(x)$ (step 208). Unless the fit is good, plotting on another probability sheet is performed and the procedure mentioned above is repeated. When comparison between the histogram and the probability density function at a step 209 shows an acceptable goodness of fit (Yes), it is then possible to apply the extreme value statistic analysis (step 211). If otherwise (No), data is again acquired by the measurement (step 213), whereon the examination mentioned above is again performed. Upon application of the extreme value statistics, the maximum values at the individual regions or locations where the measurement was performed are sequenced in the order of the smallest to the largest value and the individual maximum values are plotted on the probability sheet in accordance with $F=i/(n+1)$, being then followed by examination of the goodness of fit and determination of the distribution parameter. Subsequently, the greatest or maximum value is predicted on the basis of the recurrence period T. Finally, the maximum degree of deterioration of the mechanical component of concern is predicted on the basis of the degree of deterioration and the data base.

Figure 13:
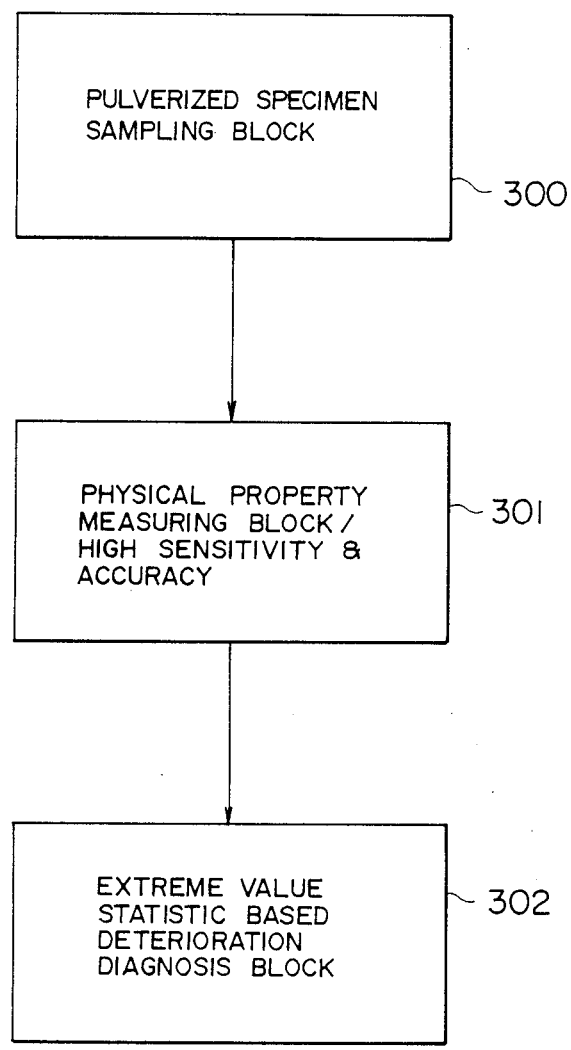
FIG. 13 is a block diagram showing a basic structure of the system according to the invention.

FIG. 13 is a block diagram showing generally a basic structure of the system according to the invention. As can be seen from this figure, the system according to the invention comprises a fine powder sampling block 300 for sampling a specimen of very small size from a mechanical component of concern constituting a part of plant, a physical property measuring block 301 of high sensitivity and high accuracy for detecting change in the physical properties of the fine specimen, and an extreme value statistical deterioration diagnosis block 302.

Figure 14:
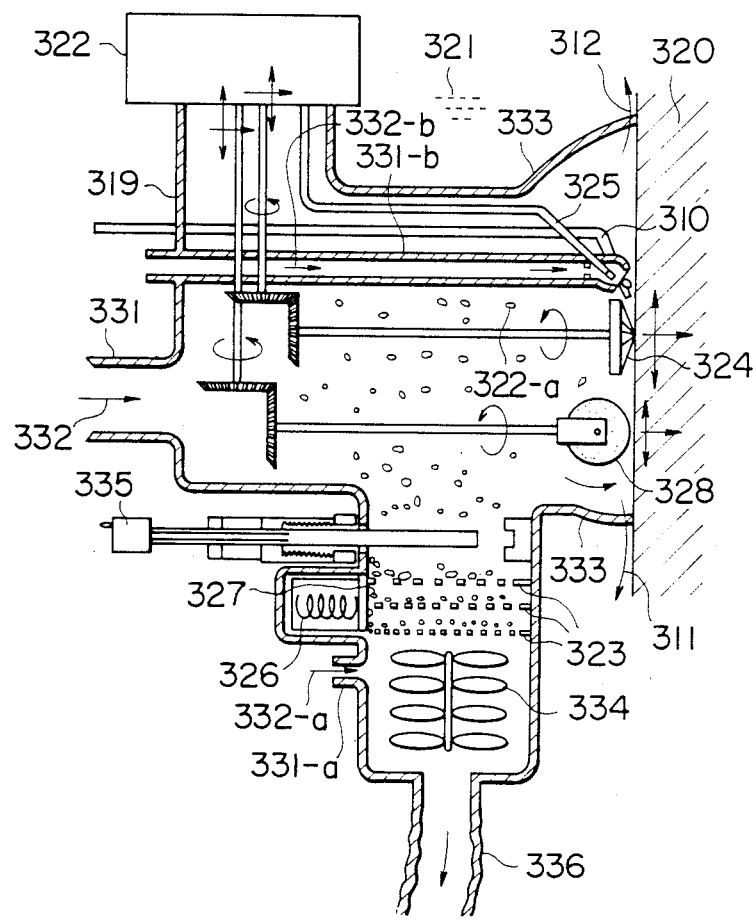
FIG. 14 is a view showing schematically a specimen sampling apparatus of vacuum pump type.
Figure 15:
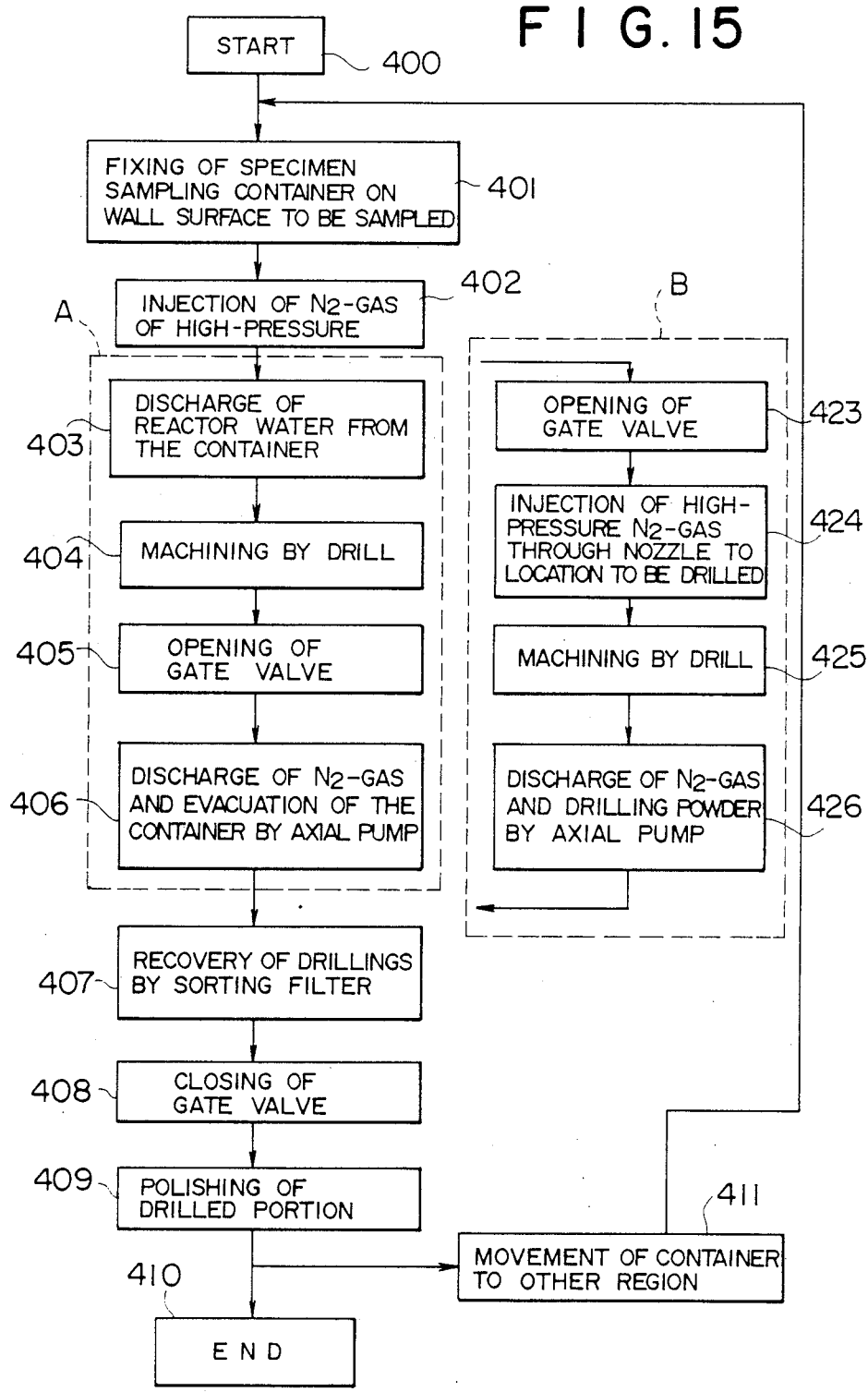
FIG. 15 is a flow chart illustrating a procedure for sampling a specimen by using the apparatus shown in FIG. 14.

FIG. 14 is a view showing schematically a specimen sampling apparatus of vacuum pump type, and FIG. 15 is a flow chart illustrating a procedure for sampling a specimen by using the apparatus shown in FIG. 14.

Referring to FIG. 15 together with FIG. 14, clads formed on the surface of a reactor wall 320 (made of stainless steel) are removed by using a water jet 310. Subsequently, a specimen sampling container 319 is fixedly mounted on the reactor wall from which the specimen is to be sampled, whereon nitrogen gas 332 of a high pressure is introduced through a first gas injection port 331. Because a skirt 333 of a rubber material is provided between the specimen sampling container 319 and the reactor vessel wall 320, water coolant 321 within the specimen sampling container 319 is discharged from the skirt 333 in the directions indicated by arrows 311 and 312 under the action of the high-pressure nitrogen gas 332, resulting in that the interior of the specimen sampling container 319 is filled with the nitrogen gas. On the side of the specimen sampling container 319 where an axial flow pump 334 is mounted, the high pressure nitrogen gas 332-a is introduced through a second gas injection port 331-a. Next, a drill 324 is operated with a gate valve 335 being opened while the pump 334 is actuated. Then, drilling powder 332-a resulting from the drill machining is discharged as carried by the high-pressure nitrogen gas to be caught by a filter 323. After having discharged the reactor water 321 from the specimen sampling container 319, the space located upstream of the pump 334 is filled with the nitrogen gas, whereon the high-pressure nitrogen gas 332-b is injected toward a location to be drilled with the axial flow pump 334 being simultaneously operated. Then, chips or powder 332-a resulting from the drilling can be effectively caught by the filter 323. Finally, the gate valve 335 is closed, and the drilled portion is polished by a grinding stone wheel 328. In case the specimen sampling process is to be further continued, the specimen sampling container 319 is moved to a region where specimen is to be sampled and the procedure is repeated.

The procedure described above is performed in accordance with the flow chart shown in FIG. 15 and including the steps shown as enclosed by a broken line block A. It should however be understood that the steps within the block A may be replaced by those enclosed in a broken line block B. In the latter case, the drill machining is effected after the gate valve has been opened.

As will be appreciated from the foregoing, the specimen sampling apparatus according to an embodiment of the invention is advantageous in that admixture of foreign materials floating on the water surface within the reactor can positively be prevented because the specimen sampling container 319 can be evacuated or filled with a gas.

As will now be appreciated, it is possible according to the present invention to sample specimens from existing mechanical components of a nuclear reactor plant without impairing or cracking the surfaces of the components while preventing positively the chips from dropping onto the bottom of the reactor. Thus, the reliability of the specimen sampling can be enhanced significantly.

Next, description is turned to an exemplary embodiment of the high-sensitivity and high-accuracy physical property measuring block for measuring the physical properties of the fine specimen sampled in the manner described above.

Figure 16:
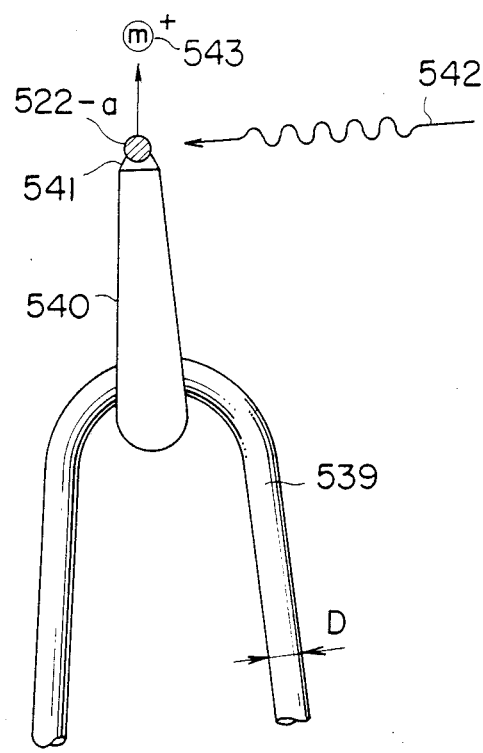
FIG. 16 is a view showing a specimen chip as sampled in the mounted state ready for an atom probe analysis.

FIG. 16 is a view showing a sampled specimen chip in the state ready for an atom probe analysis. Of the specimens actually sampled, the material actually required for the atom probe analysis may be only of an extremely small amount. Because of radioactivity of the specimen, manipulation and analysis thereof is performed under remote control. For mounting the powder chip 522-a, a loop 539 of molybdenum (Mo) is first formed by bending a Mo-wire segment of 0.25 mm in diameter D at a mid portion thereof and a metal substrate 540 of Mo is spot-welded to the bent wire at the mid portion, whereon the chip 522-a is positioned in place on the tip of the metal substrate 540 through interposition of electrically conductive adhesive film 541. When surface atoms of the chip 522-a are to be observed with the aid of a field ion microscope (FIM) featuring one aspect of the atom probe analysis, it is necessary to form the tip portion of the metal substrate 540 having the chip 522-a mounted thereon into a semi-spherical form by an ion milling or the like processing. Further, when composition analysis is to be performed in the direction depthwise from the surface of the chip 522-a, a high voltage of positive bias is applied to the specimen under ultra-high vacuum. Subsequently, the tip of the specimen chip 522-a is irradiated with a pulse laser beam 542 in the direction perpendicular to the axis of the metal substrate 540. Consequently, atoms are emitted from the surface of the chip 522-a in the form of evaporated ions 543.

Figure 17:
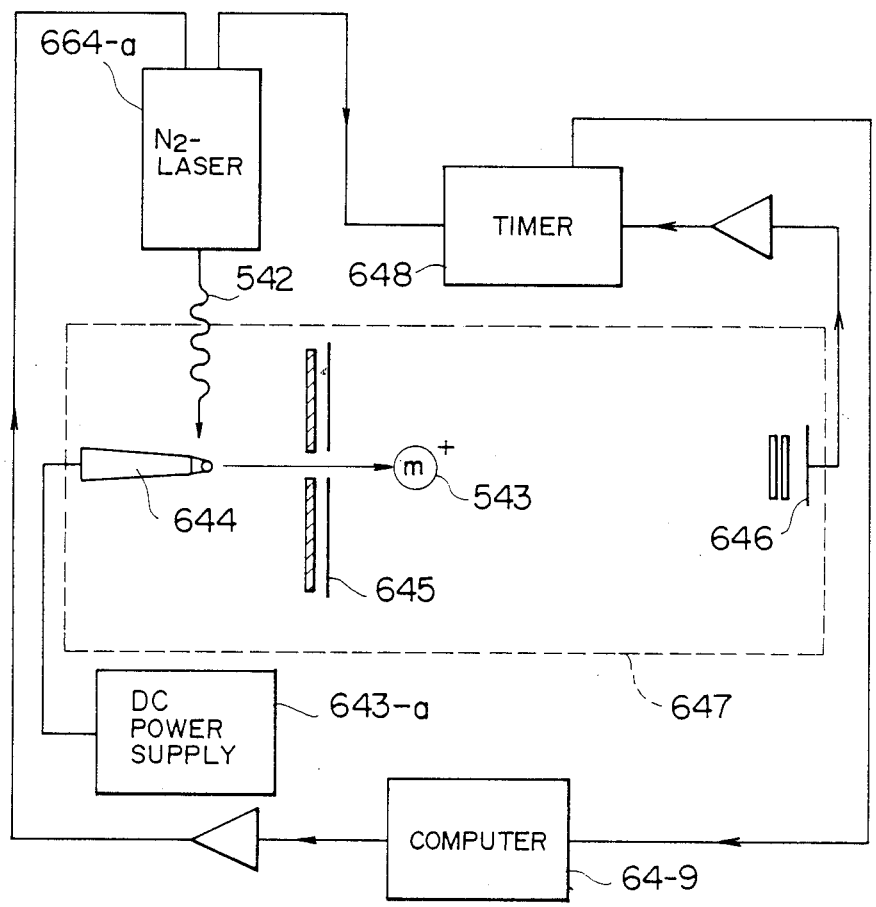
FIG. 17 is a view illustrating the principle of the atom probe analysis.

FIG. 17 is a view illustrating the principle of the atom probe analysis. When a high voltage of several kV is applied with positive bias to a specimen 644 prepared for the atom probe analysis and having the chip 522-a mounted thereon from a DC. power supply 643-a while a pulse laser beam 542 is caused to impinge onto the tip of the specimen 644-a, the surface atoms in the tip region subjected to the highest field intensity is evaporated as ions 543 which can reach a detector 646 through a center hole formed in a screen 645. The flight time of the ions is measured by a timer provided externally of a vacuum chamber 647 to thereby identify the ions 543 with the aid of the computer 649.

By performing the analysis for each specimen in accordance with the principle described above, it is possible to determine a concentration profile for each species of atoms in the direction depthwise from the outermost surface of the specimen since the detected number of ions for each species of atoms can be estimated from the material of the specimen, the applied voltage and the distance between the specimen and the screen. By applying the extreme value statistical analysis to the result thus obtained, the degree of deterioration can be estimated.

Figure 20:
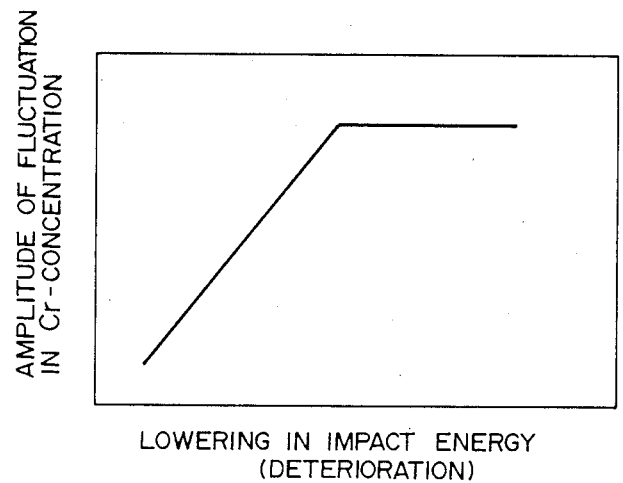
FIG. 20 is a characteristic diagram showing a relation between fluctuation in Cr-concentration and the deterioration.

FIG. 18 shows a profile of Cr-concentration in the ferrite phase of unaged duplex-phase stainless steel, and FIG. 19 shows a profile of Cr-concentration in ferrite phase of stainless steel that has undergone aging at a temperature of 475° C. for 1000 hours. Concentration of Cr of the unaged steel is stable around 28% and substantially no fluctuation can be observed. In contrast, in the case of the Cr-concentration profile of the aged stainless steel material, significant fluctuation is observed together with generation of $\alpha'$-phase and G-phase and high Cr-concentration regions. For the aged stainless steel exhibiting the Cr-concentration profile shown in FIG. 19, the degree of deterioration can be predicted or estimated on the basis of the extreme value statistical analysis described previously by referring to the data indicating the relation between the Cr-concentration and the degree of deterioration as shown in FIG. 20.

As will be understood from the foregoing description, the size and concentration of very fine precipitates providing a cause for deterioration in the strength of materials forming the existing mechanical components of the nuclear reactor can be evaluated on the order of an atomic layer to great advantage.

Next, description will be directed to an exemplary embodiment of the high-sensitivity and high accuracy physical property measuring system to which a SQUID sensor is applied according to another embodiment of the invention.

Figure 21:
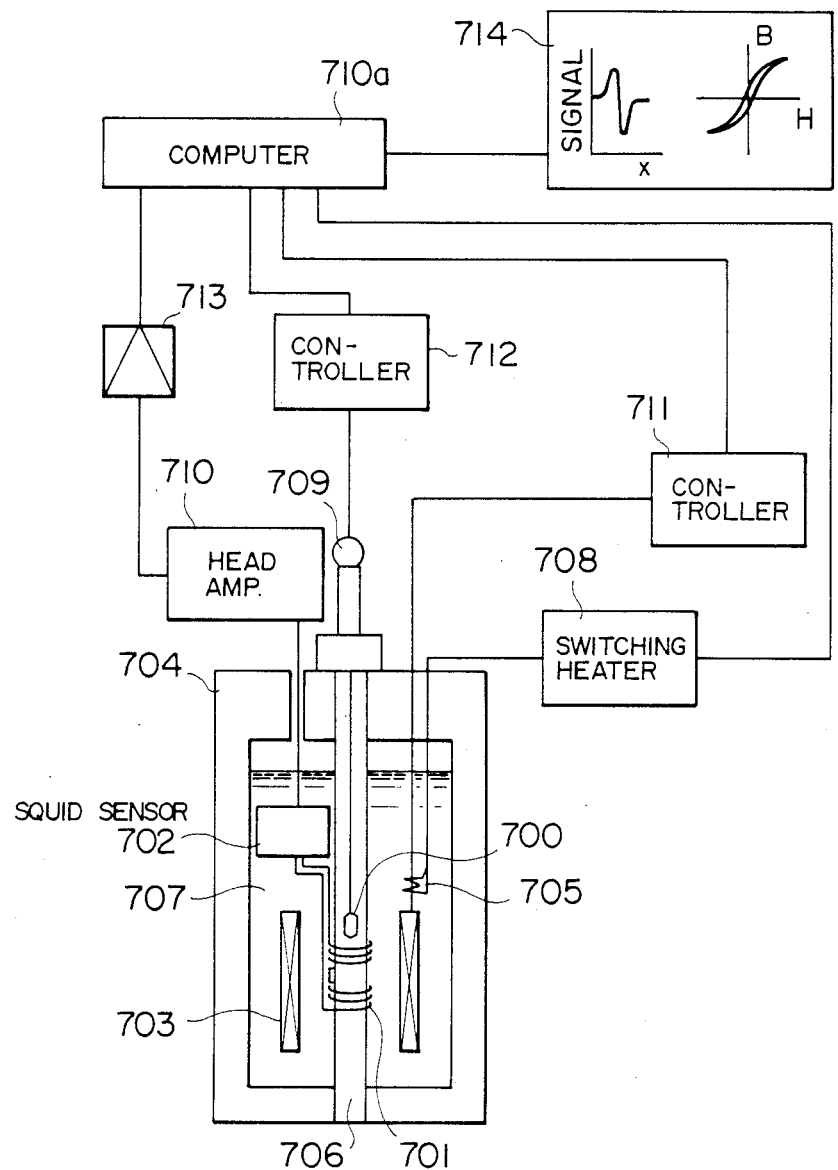
FIG. 21 is a view showing, by way of example, a structure of a physical property measuring apparatus incorporating a SQUID sensor.

FIG. 21 shows, by way of example, a structure of a system for measuring physical property of a metallic material with the aid of the SQUID sensor. In the figure, a reference numeral 700 denotes a capsule containing fine powder specimen sampled from a pipeline or other mechanical component installed in a nuclear power plant. A numeral 701 denotes a pick-up coil for detecting magnetic characteristics of the specimen to be measured, and 702 denotes the SQUID sensor. A numeral 703 denotes a superconducting excitation coil and 704 denotes a cryostat for providing a low-temperature environment for the measuring system. A numeral 705 denotes a switching heater for setting the superconducting excitation coil 703 to a permanent current mode. A numeral 706 denotes a bore employed for measurement provided at the center of the cryostat 704. A numeral 707 denotes a coolant constituted by liquid helium (He). A numeral 708 denotes a controller for the switching heater 705. A numeral 709 denotes a driving unit for moving upwardly and downwardly the capsule 700 containing the pulverized specimen. A numeral 710 denotes a head amplifier for the SQUID sensor 702. A numeral 711 denotes a controller for the superconducting excitation coil 703. A numeral 713 denotes an integrator for integrating the output of the head amplifier 10 of the SQUID sensor. All data as produced are inputted to the computer 710a equipped with a display unit 714.

Operation of the physical property measuring apparatus incorporating the SQUID sensor will now be described by reference to the drawings.

Figure 22:
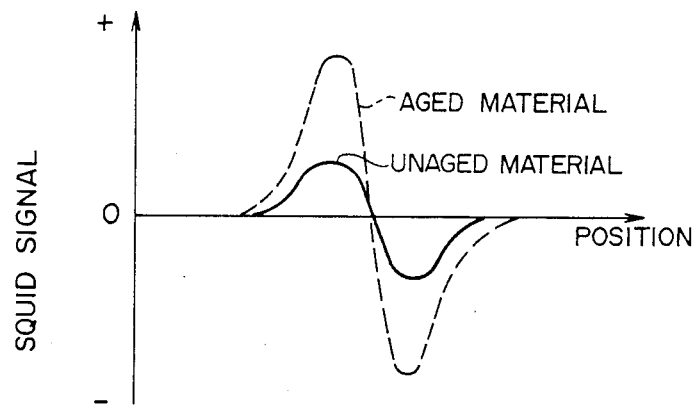
FIG. 22 is a characteristic diagram showing an example of output of a SQUID sensor.

FIG. 22 is a view for graphically illustrating the results of measurements performed on an unaged material and an aged material that has undergone deterioration. By moving upwardly and downwardly the capsule 700 under inspection by the driving unit 709, the results shown in FIG. 22 are obtained as the outputs of the SQUID sensor.

Figure 23:
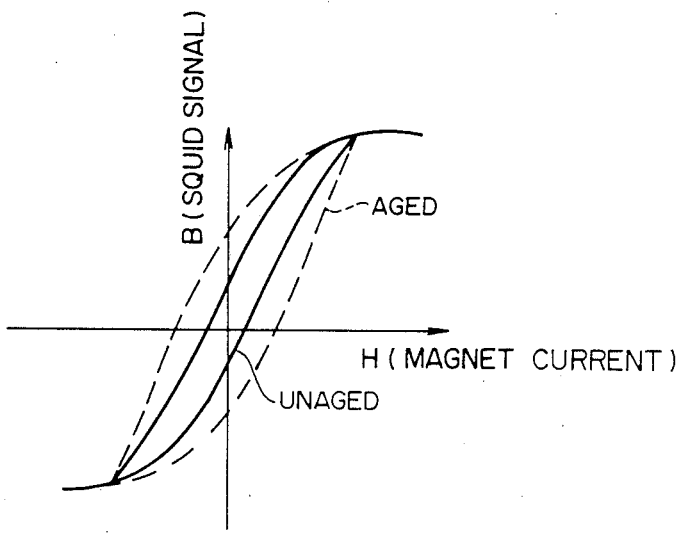
FIG. 23 is a characteristic diagram for illustrating change in B–H curve as brought about by deterioration of a material.

Further, the specimen capsule 700 is fixed in respect to the position and B-H characteristic of the specimen capsule 700 is measured by converting the current flowing through the superconducting excitation coil 703 so as to have a sinusoidal waveform. FIG. 23 shows the B-H characteristic curve as derived from the measurement.

By determining previously the data of magnetic characteristic of the specimen capsule 700 as a function of the aging thereof as well as the master curve representing the relation between the output of the SQUID sensor and the degree of embrittlement, it is possible to determine with a high accuracy the degree of embrittlement of the specimen capsule 700.

According to the present invention, it is possible to sample the specimen without impairing the structural integrity of the plant, because generation of corners and fine cracks due to the machining which may lead to deterioration of the material of the existing mechanical component of the nuclear power plant can be prevented in a satisfactory manner.

Besides, since the sizes and concentrations of very fine precipitates produced in duplex-phase stainless steel which give rise to textual deterioration in the mechanical components of the nuclear power plant due to the aging in the high-temperature environment can be determined on the basis of the specimens sampled actually from the existing mechanical members instead of one and the same piece used for the test, high accuracy and reliability can be assured for the diagnosis concerning the aging and deterioration of the parts constituting the reactor power plant.

Additionally, when the specimen sampling apparatus according to an embodiment of the invention is used, the chip resulting from the machining for sampling the specimen can be caught without any appreciable loss, influence of the residue of the specimen to the plant can completely be neglected.

Finally, since the deterioration of a machine or apparatus due to the aging can be predicted on the basis of the measurement of a part of the machine which can be performed for a short time, not only the possibility of damage and embrittlement of the existing machine can be supressed to a minimum, but also the safety of personnel and the environment can be enhanced significantly.

We claim:

1. A method for predicting the degree of deterioration of a metal member in a machine or apparatus with the aid of a computer, said metal member having a ferromagnetic phase, comprising:
   (a) a step of storing in a memory data indicating a relation between a physical property of said member to be measured and the degree of deterioration of said member;
   (b) a step of measuring said physical property of said member by sensor means at a plurality of locations within one region of said member;
   (c) a step of converting said physical property into electrical signals;
   (d) a step of inputting said electrical signals to said computer;
   (e) a step of determining by said computer the extreme value of said measured values obtained in said one region;
   (f) a step of carrying out said steps (b), (c), (d) and (e) in a plurality of regions of said member, respectively, to thereby determine the extreme values for said plurality of regions, respectively, by means of said computer;
   (g) a step of estimating an extreme value of said physical property for said member as a whole on the basis of said extreme values for said plurality of regions by applying a return period defined according to extreme value statistical theory;
   (h) a step of predicting the degree of deterioration of aid member on the basis of data stored in said memory and said estimated extreme value determined at said step (g); and
   (i) a step of recognizing results obtained by said computer in said steps (e), (f) and (g), and graphically displaying them on a display device.

2. A prediction method according to claim 1, wherein said physical property is coercive force of said part.

3. A prediction method according to claim 1, wherein said member is made of a ferrite containing stainless steel material.

4. A prediction method according to claim 1, wherein said sensor means includes at least one magnetic sensor.

5. A prediction method according to claim 1, wherein said sensor means is constituted by a sensor array capable of performing the measurements simultaneously at a plurality locations within said one region.

6. A prediction method according to claim 1, wherein said sensor means is constituted by a SQUID sensor.

7. An apparatus for predicting the degree of deterioration of a metal member in a machine or apparatus, said metal member having a ferromagnetic phase, comprising:

sensor means for measuring a magnetic property of said member, and converting the measured property into electrical signals;

memory means for storing data indicating said magnetic property of said member to be measured and the degree of deterioration of said member;

means connected to said sensor means for measuring said magnetic property in a plurality of regions of said member and for determining an extreme value of said measurements performed at a plurality of locations in each of said regions;

means for estimating the extreme value of said magnetic property of said member as a whole on the basis of the extreme values in said regions, respectively, by applying a return period defined according to extreme value statistical theory;

means for predicting the degree of deterioration of said member on the basis of the extreme value of said magnetic property of said member as a whole; and means for recognizing the extreme value or the degree of deterioration of said member, and displaying it graphically.

8. A deterioration predicting apparatus according to claim 7, said magnetic property is coercive force of said member.

9. A deterioration predicting apparatus according to claim 7, wherein said member is made of a ferrite containing stainless steel material.

10. A deterioration predicting apparatus according to claim 7, wherein said sensor means is constituted by a sensor array capable of performing the measurements simultaneously at a plurality locations within said one region.

11. A deterioration predicting apparatus according to claim 7, wherein said sensor means is constituted by a SQUID sensor.

12. An apparatus for predicting the degree of deterioration of a member in a machine or apparatus installed in a plant, said member having a ferromagnetic phase, comprising:

sampling means for sampling portions of said member as specimens at different regions of said member, wherein a plurality of specimens are obtained in each of said regions;

sensor means for measuring a metallographic property of said member, and converting the property into electrical signals;

memory means for storing data indicating a relation between said metallographic property of said member to be inspected and the degree of deterioration of said member;

means connected to said sensor means for measuring said metallographic property of said plural specimens sampled from each of a plurality of regions on said member by means of said sensor means and determining an extreme value of those resulting from measurements of the plural specimens sampled for each of said regions;

means for estimating the extreme value of said metallographic property for said member as a whole on the basis of the extreme values determined for said regions, respectively, by applying the return period defined according to extreme value statistical theory;

means for predicting the degree of deterioration of said member on the basis of the extreme value of said metallographic property estimated for said member as a whole by referencing the data stored in said memory means; and means for recognizing the extreme value or the degree of deterioration of said member, and displaying it graphically.

13. A deterioration predicting apparatus according to claim 12, wherein said specimen is sampled by machining said member by drill means.

14. A deterioration predicting apparatus according to claim 12, wherein said sampling means includes means for polishing the portion of said member from which the specimen has been obtained.

15. A deterioration predicting apparatus according to claim 12, wherein said sensor means includes a SQUID sensor.

16. A deterioration predicting apparatus according to claim 12, wherein said sensor means includes an atom probe.

17. A deterioration predicting apparatus according to claim 12, wherein said plant is a nuclear power plant.

18. A deterioration predicting apparatus according to claim 12, wherein said plant is a chemical plant.

* * * * *